United States Patent [19]

Kakiuchi et al.

[11] 4,171,970

[45] Oct. 23, 1979

[54] METHOD OF REDUCING THE LENGTH, MODERATING THE TILLERS, ADVANCING THE EARING PERIOD AND INCREASING THE YIELD OF GRAMINACEOUS PLANTS

[75] Inventors: Fumikazu Kakiuchi; Jiro Takemoto; Seiichi Maeda, all of Wakayama; Kazuhiko Kurita, Kainan; Tsuneyuki Takeno, Wakayama, all of Japan

[73] Assignee: Kao Soap Co., Ltd., Tokyo, Japan

[21] Appl. No.: 852,836

[22] Filed: Nov. 18, 1977

[30] Foreign Application Priority Data

Nov. 26, 1976 [JP] Japan .................. 51/141933

[51] Int. Cl.$^2$ .................. A01N 5/00; A01N 9/14
[52] U.S. Cl. .................. 71/88; 71/76; 71/103
[58] Field of Search .................. 71/88, 103, 76

[56] References Cited

U.S. PATENT DOCUMENTS

| 2,531,276 | 11/1950 | Klingel | 71/103 |
| 2,594,135 | 4/1952 | Denny | 71/103 |
| 2,624,662 | 1/1953 | Erickson et al. | 71/103 |
| 3,007,787 | 11/1961 | Campbell et al. | 71/103 |
| 3,044,926 | 7/1962 | Flavin et al. | 71/103 X |

OTHER PUBLICATIONS

Jansen, et al., Weeds, vol. 9, (1961), pp. 381–405.
Jansen, Weeds, vol. 13, (1965), pp. 117–123.

*Primary Examiner*—Joseph Paul Brust
*Attorney, Agent, or Firm*—Oblon, Fisher, Spivak, McClelland & Maier

[57] ABSTRACT

A composition for moderating the growth of graminaceous plants is disclosed which comprises at least one component as an effective ingredient selected from the group consisting of sulfonates and sulfuric esters having the formula $$R^1-SO_3M$$

wherein $R^1$ represents an alkyl or alkenyl group having 8 to 20 carbon atoms, an alkylaryl group containing an alkyl group of 8 to 20 carbon atoms, the residue of succinic acid esters represented by the formula $$\begin{array}{c} CH_2-COOR^2 \\ | \\ -CH-COOR^3 \end{array}$$

wherein $R^2$ and $R^3$ represent an alkyl group of 1 to 18 carbon atoms or an alkylaryl group containing an alkyl group of 1 to 18 carbon atoms, or the group $R^4O$ wherein $R^4$ represents an alkyl group of 8 to 20 carbon atoms or an alkylaryl group containing an alkyl group of 8 to 20 carbon atoms; and M represents an agriculturally acceptable organic or inorganic salt.

2 Claims, No Drawings

METHOD OF REDUCING THE LENGTH, MODERATING THE TILLERS, ADVANCING THE EARING PERIOD AND INCREASING THE YIELD OF GRAMINACEOUS PLANTS

BACKGROUND OF THE INVENTION

1. Field of the Invention

This invention relates to a composition suitable for moderating the growth of graminaceous plants. Accordingly, a primary object of the present invention is to provide a composition suitable for moderating the growth of graminaceous plants by shortening the length of plants, moderating the tillers and advancing the earing period.

Generally, graminaceous plants are tillering crops, and to moderate the tillering for the purpose of agricultural production is significantly meaningful to get an increased harvest.

2. Description of the Prior Art

In the specific situation of the rice-plant taken as an example of typical graminaceous plants, many tillers occur, but the ears are not inserted on all of them and some of them wither by the earing period. Such tillering is called non-available tillering which are very often observed among the 1st, 2nd and 3rd tillers occurring at high nodes of culms.

The occurrence of these non-available tillers varies, depending upon environmental conditions and cultivation methods, and the tillers are easy to develop in a warmer and more sufficiently fertilized place.

In a modern cultivation method for an increased harvest, it is important to secure powerful tillers as early as possible on which a necessary and sufficient amount of the ears (numbers of ears per unit area) will be inserted to get a desirable harvest, and to control the growth of subsequent non-available tillers. The rate of fertilizer application is recomended as a basal dressing, a foliar fertilizer or an ear manuring. Practically, popular cultivators use an excessive amount of fertilizer, resulting in the growth of non-available tillers. By these non-available tillers' growth, ears are made small-sized, culms are made weak to be liable to fall, and diseases in the latter period of growth, such as blighting disease easily occur, and as a result, the above harmful influences result in a decrease in a yield.

In the study leading to the present invention, a wide variety of chemicals capable of moderating the tillers of graminaceous plants, controlling the unnecessary height of plants and undesired extension of stems and leaves to get an increased yield have been studied. As a result of the study, it has been found that a composition comprising, as an effective ingredient, a sulfonate or a sulfuric ester having the following formula (I) can achieve the objective of the invention discussed above.

$$R^1-SO_3M \tag{I}$$

In the formula (I) $R^1$ represents an alkyl or alkenyl group having 8 to 20 carbon atoms, an alkylaryl group containing an alkyl group of 8 to 20 carbon atoms, the residue of succinic acid esters represented by the formula,

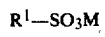

wherein $R^2$ and $R^3$ represent an alkyl group of 1 to 18 carbon atoms or an alkylaryl group containing an alkyl group of 1 to 18 carbon atoms, or the group of $R^4O—$, wherein $R^4$ represents an alkyl group of 8 to 20 carbon atoms or an alkylaryl group 8 to 20 carbon atoms; and M represents an organic or inorganic salt.

SUMMARY OF THE INVENTION

Accordingly, the present invention provides a composition which moderates the growth of graminaceous plants. The composition comprises at least one component, as an effective ingredient, selected from the group consisting of sulfonates and sulfuric esters of the formula (I).

DESCRIPTION OF THE PREFERRED EMBODIMENTS

Suitable salts represented by M in the formula (I) include inorganic salts such as potassium, sodium and calcium, and organic salts such as monoethanolamine, diethanolamine, isopropylamine and morpholine.

Suitable sulfonates of the formula (I) include sodium dodecylbenzenesulfonate, calcium dodecylbenzenesulfonate, diethanolamine dodecylbenzenesulfonate, sodium dodecylsulfonate, α-olefin sodium sulfonate, sodium dioctylsulfosuccinate and sodium diisobutylsulfosuccinate. Suitable sulfuric esters of the formula (I) include sodium laurylsulfate, sodium octylsulfate and sodium stearylsulfate.

The composition of the present invention may be used in various forms such as a powder, a wettable powder, an aqueous solution, an emulsifiable concentrate, granules, or a spray, all of which are common forms of agricultural chemicals, by adding suitable fillers to the above sulfonates or sulfuric esters.

The content of the effective ingredient according to the present invention should be in the range of 0.05 to 5.0 percent by weight, preferably 0.1 to 1.0 percent by weight.

Suitable fillers useful in the present invention include clay, kaolin, bentonite, terra abla, diatomaceous earth, calcium carbonate, methyl cellulose, starch, water, ethanol, propanol, butanol, glycols, benzene, xylene, carbonic acid gas and freon gas.

The time of applying the composition for moderating the growth of graminaceous plants according to the present invention, depends upon the variety of crops, cultivation methods, growth situations and weather conditions. In the specific situation of the rice-plant taken as an example, transplanted rice-plant develops tillers after fitness, as the number of leaves on the main culms increase, and the number of stems increase with an elapse of time. The composition may be applied preferably at the time the plants reaches an available tillering period, that is, about 30 to 35 days before the beginning of an earing period. The composition can be applied by a conventional method, for instance, by power spray or power sprinkler.

In the present invention, harmful effects of the chemicals are negligible, non-available tillering is completely suppressed, and the unnecessary height of plants and the undesired extension of stems and leaves are well controlled by applying the present composition to graminaceous plants.

As a result, the beginning of the earing period can be quickened by about one week, and an increase in the yield is obtained.

Having generally described the invention, a more complete understanding can be obtained by reference to certain specific examples, which are included for purposes of illustration only and are not intended to be limiting unless otherwise specified.

EXAMPLE 1

Emulsifiable concentrate:

To 40 parts by weight of a 70% solution of calcium dodecylbenzenesulfonate in methanol were added 30 parts by weight of polyoxyethylene (20) sorbitan monolaurate and sufficient isobutyl alcohol to obtain 100 parts by weight of the whole. At the time of use, it was diluted 200 times with water.

EXAMPLE 2

Aqueous solution:

To 80 parts by weight of a 25% aqueous solution of sodium dodecylbenzenesulfonate was added 20 parts by weight of polyoxyethylene (20) sorbitan monoolate to prepare an aqueous solution. At the time of use, it was diluted 100 times.

EXAMPLE 3

In a vessel for seed-bed measuring 33.5×48 cm were seeded rice-plants (Species, NIHONBARE) one by one at intervals of 8×9 cm on April 30, 1976 and bred till the 4th leaf stage of main stem leaves. Thereafter, they were transferred to a 1/5,000 Wagner pot on May 11, 1976. In the nurserybed stage, 8.6 g/seedbed of a conventional compound fertilizer (N:P:K=14:17:12) was applied and 1.2 g/seedbed of nitrogen was given. In the paddy field, 1.5 g of ammonium sulfate, 2.0 g of superphosphate and 0.2 g of potassium chloride per pot were given as a manure. Also, 2.0 g of ammonium sulfate and 1.0 g of potassium chloride were given. At the 13/0 leaf stage which seems to be an available tillering period, an aqueous solution having a given concentration of each test chemical was sprayed in an amount of 20 ml per pot by spray gun. The numbers of stems and main culms were counted at a certain interval, and the number of the ears was measured in the earing period. The results obtained are shown in the following table.

| Test chemicals | Concentrations (%) | Moderating effects on tillering per stub | | |
|---|---|---|---|---|
| | | maximum number of tillers | number of ears | number of non-available tillers |
| sodium dodecylbenzenesulfonate | 0.3 | 25.4 | 22.9 | 2.5 |
| calcium dodecylbenzenesulfonate | o.3 | 26.2 | 23.6 | 2.6 |
| diethanolamine dodecylbenzenesulfonate | 0.3 | 24.8 | 21.9 | 2.9 |
| sodium dodecylsulfonate | o.3 | 25.6 | 23.3 | 2.3 |
| calcium dodecylsulfonate | 0.3 | 25.8 | 23.3 | 2.5 |
| sodium di (2-ethylhexyl)-sulfosuccinate | 0.3 | 25.3 | 22.9 | 2.4 |
| α-olefin calcium sulfonate | 0.3 | 26.5 | 24.3 | 2.2 |
| α-olefin sodium sulfonate | 0.3 | 26.4 | 23.3 | 3.1 |
| sodium laurylsulfate | 0.3 | 26.6 | 23.7 | 2.9 |
| sodium stearylsulfate | 0.3 | 26.6 | 23.1 | 3.2 |
| sodium dodecylbenzenesulfonate | 1.0 | 23.5 | 21.0 | 2.5 |
| calcium dodecylbenzenesulfonate | 1.0 | 24.2 | 21.8 | 2.4 |
| sodium dodecylsulfonate | 1.0 | 23.8 | 21.0 | 2.8 |
| sodium laurylsulfate | 1.0 | 24.8 | 21.9 | 2.9 |
| ⌈ calcium dodecylbenzenesulfonate | 0.3 | 25.6 | 22.6 | 3.0 |
| ⌊ sodium laurylsulfate | 0.5 | | | |
| ⌈ sodium dodecylbenzenesulfonate | 0.3 | 25.8 | 22.6 | 3.2 |
| ⌊ sodium laurylsulfate | 0.5 | | | |
| ⌈ calcium dodecylbenzenesulfonate | 0.3 | 26.0 | 23.2 | 2.8 |
| ⌊ α-olefin sodium sulfonate | 0.2 | | | |
| ⌈ sodium dodecylsulfonate | 0.3 | 25.5 | 22.3 | 3.2 |
| ⌊ sodium laurylsulfate | 0.2 | | | |
| ⌈ sodium di (2-ethylhexyl)-sulfosuccinate | 0.2 | 25.9 | 22.8 | 3.1 |
| ⌊ sodium laurylsulfate | | | | |
| ⌈ α-olefin sodium sulfonate | 0.3 | 26.2 | 23.2 | 2.9 |
| ⌊ sodium di (2-ethylhexyl)-sulfosuccinate | 0.2 | | | |
| Untreated (control) | — | 26.8 | 19.4 | 7.4 |

What is claimed as new and intended to be secured by Letters Patent is:

1. A method of reducing the length, moderating the tillers, advancing the earing period and increasing the yield of graminaceous plants which comprises applying to said graminaceous plants an effective amount of a composition comprising as its sole agent effective to reduce the length, moderate the tillers, advance the earing and increase the yield of said graminaceous plants from 0.05 to 5 wt.% of at least one component selected from the group consisting of sulfonates and sulfuric esters represented by the formula $$R^1-SO_3M$$

wherein $R^1$ represents an alkyl or alkenyl group having 8 to 20 carbon atoms, an alkylbenzyl group containing an alkyl group of 8 to 20 carbon atoms, the residue of succinic acid esters represented by the formula $$\begin{array}{c} CH_2-COOR^2 \\ | \\ -CH-COOR^3 \end{array}$$

wherein $R^2$ and $R^3$ represent an alkyl group of 1 to 18 carbon atoms or an alkylbenzene group containing an alkyl group of 1 to 18 carbon atoms, or the group $R^4O-$, wherein $R^4$ represents an alkyl group of 8 to 20 carbon atoms or an alkylbenzene group containing an alkyl group of 8 to 20 carbon atoms; and M is selected from the group consisting of potassium, sodium, calcium, monoethanolamine, diethanolamine, isopropylamine and morpholine; and an inert diluent.

2. The method of claim 1, wherein said graminaceous plants are rice-plants and said composition is applied to said rice-plants at an available tillering period.

* * * * *